United States Patent [19]

Bernardi et al.

[11] Patent Number: 4,746,666
[45] Date of Patent: May 24, 1988

[54] ERGOLINE COMPOUNDS USEFUL AS ANTIPARKINSON AGENTS

[75] Inventors: Luigi Bernardi; Sergio Mantegani; Aldemio Temperilli, all of Milan; Gabriella Traquandi, Cornate d'Adda; Alessandro Rossi, Milan, all of Italy

[73] Assignee: Farmitalia Carlo Erba S.p.A., Milan, Italy

[21] Appl. No.: 874,413

[22] Filed: Jun. 16, 1986

[30] Foreign Application Priority Data

Jun. 19, 1985 [GB] United Kingdom ............... 8515528

[51] Int. Cl.⁴ .................... A61K 31/48; C07D 457/04
[52] U.S. Cl. ...................... 514/288; 546/67; 546/68
[58] Field of Search ............... 546/67, 68; 514/288

[56] References Cited

U.S. PATENT DOCUMENTS

| | | | |
|---|---|---|---|
| 3,647,655 | 3/1972 | Bernardi et al. | 204/157.71 |
| 4,180,581 | 12/1979 | Stadler | 546/69 |
| 4,500,712 | 2/1985 | Bernardi et al. | 546/68 |
| 4,690,929 | 9/1987 | Bernardi et al. | 546/68 |

FOREIGN PATENT DOCUMENTS 0070562 1/1983 European Pat. Off. .
0091652 10/1983 European Pat. Off. .

OTHER PUBLICATIONS

Bernardi et al, CA 74-42536n.
The Journal of the American Chemical Society, vol. 83, 1961, W. S. Wadsworth et al., "The Utility of Phosphonate Carbanions in Olefin . . . ", pp. 1733–1738.

Primary Examiner—Donald G. Daus
Assistant Examiner—Cecilia Shen
Attorney, Agent, or Firm—Oblon, Fisher, Spivak, McClelland & Maier

[57] ABSTRACT

Ergoline derivatives of the formula I

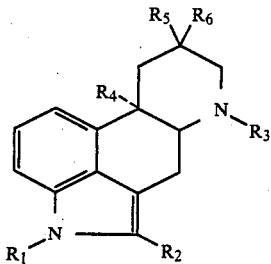

wherein $R_1=H, CH_3$; $R_2=H$, halogen, $CH_3$, CN, $C_1-C_4$ alkylthio or phenylthio; $R_3=C_1-C_4$ hydrocarbon; $R_4=H$, $OCH_3$; $R_5=H$ and $R_6=-CH=CH-CONHR_7$ or $R_5$ and $R_6=\!=\!CH-CONHR_7$; $R_7=$2-thiazolyl, 3-pyridazinyl, 1,3,4-thiadiazol-2-yl or 4-pyrimidinyl group optionally substituted, and pharmaceutically acceptable salts thereof, display activity on the Central Nervous System and are useful as antiprolactinic agents. Their preparation and pharmaceutical compositions containing them are also described.

4 Claims, No Drawings

ERGOLINE COMPOUNDS USEFUL AS ANTIPARKINSON AGENTS

BACKGROUND OF THE INVENTION

1. Field of the Invention

The invention relates to ergoline derivatives, to a process for their preparation and to pharmaceutical compositions containing them.

2. Discussion of the Background

The ergot alkaloids are important pharmaceutical compounds. Ergot alkaloids are obtained by isolation from the crude ergot grown in the field, extraction from saprophytic cultures or from partial and total synthesis. Ergoline derivatives are active central nervous system agents.

SUMMARY OF THE INVENTION

An object of the present invention is to provide novel ergoline derivatives which are effective in the central nervous system.

Another object of the invention is to provide novel ergoline derivatives which are effective in the central nervous system and are useful antiparkinson agents.

A further object of the invention is to provide novel ergoline derivatives which exhibit moderate to good antiprolactinic activity.

A further object of the invention is to provide a pharmaceutical composition containing a novel ergoline derivative and a suitable pharmaceutical carrier or excipient.

A further object of the invention is to provide a process for the preparation of novel ergoline derivatives.

These objects and other objects which will become apparent from the following specification have been met by the ergoline derivatives, process for their preparation and pharmaceutical compositions containing them of the present invention. The invention provides ergoline derivatives having the general formula I.

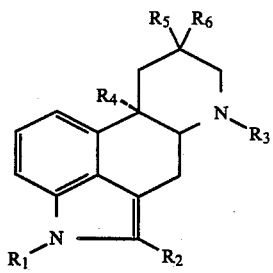

DETAILED DESCRIPTION OF THE PREFERRED EMBODIMENTS

In the formula I, $R_1$ represents a hydrogen atom or a methyl group.

$R_2$ represents a hydrogen or halogen atom, a methyl or cyano group, an alkylthio group having from 1 to 4 carbon atoms or a phenylthio group.

$R_3$ represents a hydrocarbon group having from 1 to 4 carbon atoms or a phenylthio group.

$R_4$ represents a hydrogen atom or a methoxy group.

$R_5$ represents a hydrogen and $R_6$ represents a group of the formula $-CH=CH-CONHR_7$, where $R_7$ represents a 2-thiazolyl, 3-pyridazinyl, 1,3,4-thiadiazol-2-yl or 4-pyrimidinyl group optionally substituted by one or more halogen atoms, alkyl groups having from 1 to 4 carbon atoms, alkoxy groups having from 1 to 4 carbon atoms, dialkylamino groups in which each alkyl group has from 1 to 4 carbon atoms, cyano or nitro groups. Alternatively $R_5$ and $R_6$ taken together may represent a group of the formula $=CHCONHR_7$, where $R_7$ is as defined above. The invention further provides pharmaceutically acceptable salts of such ergoline derivatives.

The term "halogen" is used to encompass fluorine, chlorine and bromine atoms, but chlorine and bromine atoms are preferred. The term "hydrocarbon group" is intended to include alkyl, cycloalkyl, alkylcycloalkyl, alkenyl and alkynyl groups. Representative examples are methyl, ethyl, n-propyl, i-propyl, n-butyl, t-butyl, i-butyl, methylcyclopropyl, allyl and propargyl groups. "Pharmaceutically acceptable salts" refers to those salts which retain the biological effectiveness and properties of the free bases and which are not biologically or otherwise undesirable. Such salts may be formed with inorganic acids such as hydrochloric, hydrobromic, sulphuric, nitric and phosphoric acids; or with organic acids such as acetic, propionic, glycolic, pyruvic, oxalic, malic, malonic, succinic, maleic, fumaric, tartaric, citric, benzoic, cinnamic, mandelic, methanesulphonic, ethanesulphonic, p-toluenesulphonic and salicyclic acids.

The compounds according to the invention may be prepared by reacting a carboxylic acid of the general formula II

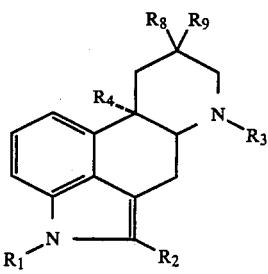

where $R_1$, $R_2$, $R_3$ and $R_4$ are as defined above and either $R_8$ represents a hydrogen atom and $R_9$ represents a carboxyvinylene group or $R_8$ and $R_9$ together represent a carboxymethylene group, or a reactive derivative of such a carboxylic acid, with an amine of the formula $R_7NH_2$ wherein $R_7$ is as defined above. This process is within the scope of the invention.

A suitable reactive derivative of the carboxylic acid II is a mixed anhydride with trifluoroacetic acid. This can be prepared by reacting the carboxylic acid II with trifluoroacetic anhydride in an inert solvent such as tetrahydrofuran, dioxane or acetonitrile at a temperature from $-20°$ to $0°$ C. for some minutes. The reaction of the mixed anhydride with the amine $R_7NH_2$, may be effected at from $-20°$ to $0°$ C. in the presence of a tertiary organic base such as pyridine or triethylamine. The final condensation products are then purified by known procedures, usually chromatography or crystallization from a suitable solvent.

The carboxylic acids II may be prepared by condensing compounds of the general formula III

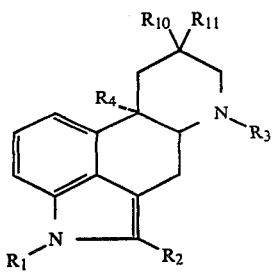

where $R_1$, $R_2$, $R_3$ and $R_4$ are as defined above, and either $R_{10}$ represents a hydrogen atom and $R_{11}$ represents a formyl group or $R_{10}$ and $R_{11}$ together represent an oxo group, with the sodium salts of trialkylphosphono acetates, according to the Horner-Emmons procedure (JACS (1961) 83, 1733, Tetrahedron 1978, 34 (7), 997). The condensation process is suitably carried out in a solvent such as dioxane, tetrahydrofuran or dimethoxyethane, at a temperature of from −20° to 0° C. for 3 hours affording the unsaturated alkyl esters. The carboxylic acids II can be obtained in good yield by alkaline saponification of the esters.

It is to be understood that Z and E isomers may be formed and that they may be separated by chromatography or fractional crystallization.

Optionally, the ergoline derivatives I where $R_4$ represents a hydrogen atom may be converted into the corresponding ergoline derivatives I where $R_4$ represents a methoxy group by photochemical methoxylation, according to known procedures.

The preparation of the starting compounds of formula III is described in Belgian Patent No. 900,228.

The ergoline derivatives according to the invention and their pharmaceutically acceptable salts are effective in the central nervous system (CNS) and are particularly useful as antiparkinson agents. They also display from moderate to good antiprolactinic activity. The prolactin secretion inhibition activity is indicated by an inhibition of fertilized eggs in the uterus on day 5 after insemination of female rats (according to the principles of E. Fluckiger et al, HNAD. EXP. PHARMAC, 49, 615, 1978).

As already stated above, the ergoline derivatives according to the invention are active in the central nervous system. In particular, they exhibit dopaminergic activity. The dopaminergic activity is indicated, e.g., by an induction of contralateral turning in rats with unilateral 6-hydroxy dopamine-induced lesions of the dopaminergic nigrostriatal pathway (According to the principles of U. Ungerstedt et al., Brain Research 24 (1970); p. 485).

The products according to the present invention have a surprisingly higher activity as compared with the known standard reference drug, Bromocriptine, as the following table shows:

| EFFECTS OF A SINGLE TREATMENT ON TURNING BEHAVIOR IN RATS | | | | |
|---|---|---|---|---|
| Product of example | Dose mg/kg | Turning rats Treated rats | Number of controlateral turns (X) in 8 hours | Route of Administration |
| 1 | 0.5 | 17/18 | 1,531 | i.p. |
| 7 | 0.5 | 5/8 | 732 | i.p. |
| 8 | 0.5 | 3/4 | 528 | i.p. |
| Bromo- | 1.0 | 4/8 | 411 | i.p. |

| EFFECTS OF A SINGLE TREATMENT ON TURNING BEHAVIOR IN RATS | | | | |
|---|---|---|---|---|
| Product of example | Dose mg/kg | Turning rats Treated rats | Number of controlateral turns (X) in 8 hours | Route of Administration |
| criptine Saline | — | 0/10 | 5 | s.c. |

The compounds are therefore indicated for use as antiparkinson agents. Administration of the active compounds and salts described herein can be via any of the accepted modes of administration for compounds having similar pharmacological activities to those cited above, and at similar dosages. The amount of active compound will, of course, be dependent on the subject being treated, the severity of the application, the manner of administration and the judgment of the prescribing physician. An indicated daily dosage is in the range from about 0.1 to about 25 mg conveniently given in divided doses 1 to 5 times a day. The methods of administration include oral and parenteral modes, preferably oral administration. For example, for the treatment of Morbus Parkinson a suitable dosage is, for oral administration to adult humans, in the range of about 0.5 to 10 mg, conveniently given in divided doses 2 to 4 times a day in unit dosage form containing from about 0.15 to about 5 mg of the compound or in sustained release form.

Accordingly, the invention also provides a pharmaceutical composition comprising an ergoline derivative having the general formula I or a pharmaceutically acceptable salt thereof in admixture with a pharmaceutically acceptable diluent or carrier. Depending on the intended mode, such compositions may be formulated in conventional manner so as to be, for example, a solution or a tablet.

The composition will include a conventional pharmaceutical carrier or excipient and an active compound of formula I or a pharmaceutically acceptable salt thereof and, in addition, may include other medicinal agents, pharmaceutical agents, carriers, adjuvants, etc. For solid compositions, conventional non-toxic solid carriers include pharmaceutical grades of mannitol, lactose, starch, magnesium stearate, sodium saccharin, talcum, cellulose, glucose, sucrose and magnesium carbonate. Liquid pharmaceutically administerable compositions can, for example, be prepared by dissolving or dispersing an active compound as defined above and an optional pharmaceutical adjuvant in a carrier, such as, for example, water, saline, aqueous dextrose, glycerol, or ethanol to thereby form a solution or suspension.

Other features of this invention will become apparent in the course of the following descriptions of exemplary embodiments which are given for illustration of the invention and are not intended to be limiting thereof.

The following Examples illustrate the invention.

EXAMPLE 1

(E)-6-Methyl-8β-[N-(6-chloro-3-pyridazinyl)-carbamoylvinylene]-ergoline

A solution of 2.7 g (0.011 mole) of triethylphosphono acetate sodium salt and 2.54 g (0.01 mole) of 6-methyl-8β-formyl-ergoline in 200 ml of tetrahydrofuran was stirred for 3 hours at 0° C. The resulting solution was poured into brine and the precipitate was extracted with ethyl acetate. Removal of the solvent and crystallization from acetone afforded 2.7 g of (E)-6-methyl-8β-ethoxy-carbonylvinylene-ergoline, m.p. 203°-205° C.

A solution of 3.2 g of this ester in 50 ml of ethanol and 0.8 g (0.02 mole) of sodium hydroxide was heated at 80° C. for 30 minutes. This solution was acidified with 20 ml of 0.1 M hydrochloric acid (0.02 mole) and then poured into iced water. The resulting precipitate was filtered off, washed with water and then with acetone, and dried to give 2.4 g of (E)-6-methyl-8β-carboxyvinylene-ergoline, m.p. 288°-290° C.

To a suspension of 2.96 g (0.01 mole) of (E)-6-methyl-8β-carboxyvinylene-ergoline in 20 ml of anhydrous acetonitrile at −20° C. was added dropwise a solution of 4.3 g (0.015 mole) of trifluoroacetic anhydride in 10 ml of acetonitrile under stirring. After 10 minutes at −20° C., 1.29 g (0.01 mole) of 3-amino-6-chloro-pyridazine in 20 ml of pyridine was added and the reaction mixture was stirred at between −10° C. and 0° C. for 15 minutes. The resulting solution was poured into ethyl acetate and extracted several times with a 10% ammonium hydroxide solution. The organic phase was washed with brine, dried and evaporated to dryness. The residue, crystallized from methanol, gave 2.5 g of the title compound, m.p. 273°-275° C.

EXAMPLE 2

(E)-6-Methyl-8β-[N-(5-methyl-1,3,4-thiadiazol-2-yl)carbamoylvinylene]-ergoline

Operating as in Example 1, but employing 2-amino-5-methyl-1,3,4-thiadiazole in place of 3-amino-6-chloro-pyridazine, the title compound was obtained in 65% yield, m.p. 275°-277° C.

EXAMPLE 3

(E)-6-Methyl-8β-[N-(2-thiazolyl)-carbamoylvinylene]-ergoline

Operating as in Example 1, but employing 2-aminothiazole in place of 3-amino-6-chloro-pyridazine, the title compound was obtained in 60% yield, m.p. 250°-251° C.

EXAMPLE 4

(E)-6-Methyl-8β-[N-(3-pyridazinyl)-carbamoylvinylene]-ergoline

Operating as in Example 1, but employing 3-aminopyridazine in place of 3-amino-6-chloro-pyridazine, the title compound was obtained in 40% yield, m.p. 260°-262° C.

EXAMPLE 5

(E)-6-Methyl-8β-[N-(2,6-dimethyl-4-pyrimidinyl)carbamoylvinylene]-ergoline

Operating as in Example 1, but employing 2,6-dimethyl-4-amino-pyrimidine in place of 3-amino-6-chloro-pyridazine, the title compound was obtained in 39% yield, m.p. 273°-275° C.

EXAMPLE 6

(E)-6-Ethyl-8β-[N-(6-chloro-3-pyridazinyl)-carbamoylvinylene]-ergoline

Operating as in Example 1, but employing 6-ethyl-8β-formyl-ergoline in place of 6-methyl-8β-formylergoline, (E)-6-ethyl-8β-ethoxycarbonylvinylene-ergoline was obtained, m.p. 185°-187° C. From this, (E)-6-ethyl-8β-carboxyvinylene-ergoline was obtained, m.p. 204°-205° C., and finally the title compound was obtained in 45% yield, m.p. 227°-229° C.

EXAMPLE 7

(E)-6-Allyl-8β-[N-(6-chloro-3-pyridazinyl)-carbamoylvinylene]-ergoline

Operating as in Example 1, but employing 6-allyl-8β-formyl-ergoline in place of 6-methyl-8β-formyl-ergoline, (E)-6-allyl-8β-ethoxycarbonylvinylene-ergoline was obtained, m.p. 153°-155° C. From this (E)-6-allyl-8β-carboxyvinylene-ergoline was obtained, m.p. 205°-207° C., and finally the title compound was obtained in 40% yield m.p. 220°-222° C.

EXAMPLE 8

(E)-6-Propyl-8β-[N-(6-chloro-3-pyridazinyl)-carbamoylvinylene]-ergoline

Operating as in Example 1, but employing 6-propyl-8β-formyl-ergoline in place of 6-methyl-8β-formyl-ergoline, (E)-6-propyl-8β-ethoxycarbonylvinylene-ergoline, ergoline was obtained, m.p. 170°-173° C. From this (E)-6-propyl-8β-carboxyvinylene-ergoline was obtained, m.p. 190°-192° C., and finally the title compound was obtained in 50% yield m.p. 200°-202° C.

EXAMPLE 9

(Z)-6-Methyl-8β-[N-(6-chloro-3-pyridazinyl)-carbamoylvinylene]-ergoline

Operating as in Example 1, but employing 2-ethoxycarbonylmethyl-4,5-dimethyl-2-oxo-1,3,2-dioxaphospholane in place of triethylphosphonoacetate, (Z)-6-methyl-8β-ethoxycarbonylvinylene-ergoline was obtained, m.p. 208°-210° C. From this (Z)-6-methyl-8β-carbonylvinylene-ergoline was obtained, m.p. 268°-270° C., and finally the title compound was obtained in 30% yield m.p. 257°-260° C.

EXAMPLE 10

(E)-6-Methyl-8-[N-(6-chloro-3-pyridazinyl)-carbamoylmethylene]-ergoline

Operating as in Example 1, but employing 6-methyl-8-oxo-ergoline in place of 6-methyl-8β-formyl-ergoline, (E)-6-methyl-8-ethoxycarbonylmethylene-ergoline was obtained, m.p. 170°-171° C. From this (E)-6-methyl-8-carboxymethylene-ergoline was obtained, m.p. 270°-275° C., and finally the title compound was obtained m.p. 251°-253° C.

EXAMPLE 11

(Z)-6-Methyl-8-[N-(6-chloro-3-pyridazinyl)-carbamoylmethylene]-ergoline

The mother liquid obtained in Example 10, after separation of the (E)-6-methyl-8-ethoxycarbonyl-methylene-ergoline, was chromatographed on silica gel using ethyl acetate:cyclohexane:n-butanol, 4:2:1 by volume, as eluent to give (Z)-6-methyl-8-ethoxycarbonylmethylene-ergoline, m.p. 168°-170° C. From this (Z)-6-methyl-8-carboxymethylene-ergoline was obtained, m.p. 233°-235° C., and finally the title compound was obtained, m.p. 242°-243° C.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An ergoline compound of the formula I,

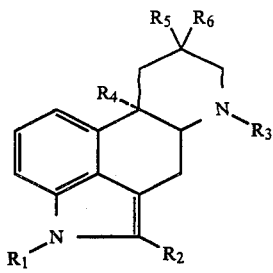

I wherein
$R_1$ represents a hydrogen atom or a methyl group;
$R_2$ represents a hydrogen or halogen atom, a methyl or cyano group, an alkylthio group having from 1 to 4 carbon atoms or a phenylthio group;
$R_3$ represents a hydrocarbon group selected from the group consisting of alkyl, cycloalkyl, alkylcycloalkyl, alkenyl, and alkyynyl groups having from 1 to 4 carbon atoms;
$R_4$ represents a hydrogen atom or a methoxy group; and either
(i) $R_5$ represents a hydrogen atom and $R_6$ represents a group of the formula —CH=CH—CONHR$_7$, wherein $R_7$ represents a 2-thiazolyl, 3-pyridazinyl, 1,3,4-thiadiazol-2-yl or 4-pyrimidinyl group unsubstituted or substituted by one or two halogen atoms, alkyl groups having from 1 to 4 carbon atoms, alkoxy groups having from 1 to 4 carbon atoms, alkylthio groups having from 1 to 4 carbon atoms, dialkylamino groups in which each alkyl groups has from 1 to 4 carbon atoms, or
(ii) $R_5$ and $R_6$ taken together represent a group of the formul =CHCONHR$_7$, wherein $R_7$ is as defined above; or a pharmaceutically acceptable salt thereof.

2. The ergoline derivative of claim 1, wherein $R_1$, $R_2$ and $R_4$ each represent a hydrogen atom, $R_3$ represents a methyl, ethyl, propyl or allyl group and wherein $R_7$ represents a 2-thiazolyl, 3-pyridazinyl, 1,3,4-thiadiazol-2-yl or 4-pyrimidinyl group substituted by one or two halogen atoms or alkyl groups having from 1 to 4 carbon atoms; or a pharmaceutically acceptable salt thereof.

3. The ergoline derivative of claim 1, wherein said derivative is
(E)-6-methyl-8β-[N-(6-chloro-3-pyridazinyl)-carbamoylvinylene]-ergoline,
(E)-6-methyl-8β-[N-(5-methyl-1,3,4-thiadiazol-2-yl)-carbamoylvinylene]-ergoline,
(E)-6-methyl-8β-[N-(2-thiazolyl)-carbamoylvinylene]-ergoline,
(E)-6-methyl-8β-[N-(3-pyridazinyl)-carbamoylvinylene]-ergoline,
(E)-6-methyl-8β-[N-(2,6-dimethyl-4-pyrimidinyl]-carbamoylvinylene]-ergoline,
(E)-6-ethyl-8β-[N-(6-chloro-3-pyridazinyl)-carbamoylvinylene]-ergoline,
(E)-6-allyl-8β-[N-(6-chloro-3-pyridazinyl)-carbamoylvinylene]-ergoline,
(E)-6-propyl-8β-[N-(6-chloro-3-pyridazinyl)-carbamoylvinylene]-ergoline,
(Z)-6-methyl-8β-[N-(6-chloro-3-pyridazinyl)-carbamoylvinylene]-ergoline,
(E)-6-methyl-8-[N-(6-chloro-3-pyridazinyl)-carbamoylmethylene]-ergoline, or
(Z)-6-methyl-8-[N-(6-chloro-3-pyridazinyl)-carbamoylmethylene]-ergoline,
or a pharmaceutically acceptable salt thereof.

4. A pharmaceutical composition comprising an ergoline derivative of claim 1 or a pharmaceutically acceptable salt thereof in an amount sufficient to display activity on the central nervous system, in admixture with a pharmaceutically acceptable diluent or carrier.

* * * * *